(12) United States Patent
Sorgente et al.

(10) Patent No.: US 10,780,068 B2
(45) Date of Patent: Sep. 22, 2020

(54) METHODS AND COMPOSITIONS FOR IMPROVING EYE HEALTH

(71) Applicants: Nino Sorgente, Washington, DC (US); Gabriele Thumann, Chen-Bougeries (CH)

(72) Inventors: Nino Sorgente, Washington, DC (US); Gabriele Thumann, Chen-Bougeries (CH)

(*) Notice: Subject to any disclaimer, the term of this patent is extended or adjusted under 35 U.S.C. 154(b) by 0 days.

(21) Appl. No.: 15/970,776

(22) Filed: May 3, 2018

(65) Prior Publication Data

US 2018/0318239 A1 Nov. 8, 2018

Related U.S. Application Data

(60) Provisional application No. 62/502,268, filed on May 5, 2017.

(51) Int. Cl.

| A61K 31/18 | (2006.01) |
| A61K 9/00 | (2006.01) |
| A61P 27/06 | (2006.01) |
| A61K 9/08 | (2006.01) |
| A61K 47/38 | (2006.01) |
| A61K 9/10 | (2006.01) |
| C12Q 1/6883 | (2018.01) |
| C12Q 1/6827 | (2018.01) |

(52) U.S. Cl.
CPC ............ *A61K 31/18* (2013.01); *A61K 9/0019* (2013.01); *A61K 9/0048* (2013.01); *A61K 9/0051* (2013.01); *A61K 9/08* (2013.01); *A61K 9/10* (2013.01); *A61K 47/38* (2013.01); *A61P 27/06* (2018.01); *C12Q 1/6883* (2013.01); *C12Q 1/6827* (2013.01); *C12Q 2600/156* (2013.01)

(58) Field of Classification Search
CPC .... A61K 31/18; A61K 9/0019; A61K 9/0048; A61K 9/0051; A61K 9/08; A61K 9/10; A61K 47/38; A61P 27/06; C12Q 1/6883; C12Q 1/6827; C12Q 2600/156
See application file for complete search history.

(56) References Cited

U.S. PATENT DOCUMENTS

| 5,629,345 | A | * | 5/1997 | Sorgente | ............... | A61K 31/121 |
| | | | | | | 514/592 |
| 5,965,620 | A | * | 10/1999 | Sorgente | ............... | A61K 31/121 |
| | | | | | | 514/592 |
| 8,143,254 | B2 | | 3/2012 | Abbott et al. | | |
| 8,354,452 | B2 | | 1/2013 | Polak et al. | | |
| 8,980,952 | B2 | | 3/2015 | Simard et al. | | |
| 9,050,345 | B2 | | 7/2015 | Finlay et al. | | |
| 9,107,932 | B2 | | 8/2015 | Simard et al. | | |
| 10,052,280 | B2 | | 8/2018 | Jacobson | | |
| 10,058,557 | B2 | | 8/2018 | Cowen | | |
| 10,085,998 | B2 | | 10/2018 | Cowen et al. | | |
| 2018/0326016 | A1 | | 11/2018 | Poeschla et al. | | |
| 2018/0327381 | A1 | | 11/2018 | De Long et al. | | |

FOREIGN PATENT DOCUMENTS

WO 2018187503 10/2018

OTHER PUBLICATIONS

Polak et al. Orphanet Journal of Rare Diseases 2007, 2:12 (Year: 2007).*
Liu et al. Diabetologia. Dec. 2013; 56(12): 2609-2618 (Year: 2013).*
Babiker et al. Diabetologia (2016) 59:1162-1166 (Year: 2016).*
Koo et al. Diabetic Medicine, 24, 178-186, 2007 (Year: 2007).*
Stein Study, at online address www.sciencedaily.com/releases/2011/08/110817120237.htm, published Aug. 17, 2011 (Year: 2011).*
Haghvirdizadeh et al. Journal of Diabetes Research vol. 2015, Article ID 908152, 9 pages (Year: 2015).*
Lin Y-W et al. Destabilization of ATP-sensitive potassium channel activity by novel mutations identified in congenital hyperinsulinism. J. Biol Chem. 2008; 283:9146-9156.
Sorensen CM, et al. Role of vascular potassium channels in the regulation of renal hemodynamics. Am J Physiol Renal Physiol. 2012;302:F505-18.
Caffes N, Kurland DB, Gerzanich V, Simard JM. Glibenclamide for the treatment of ischemic and hemorrhagic stroke. Int J Mol Sci. 2015;16:4973-84.
Pallan TV, Ahmed (.Glyburide in Treating Malignant Cerebral Edema. Blocking Sulfonyl Urea One (SUR1) Receptors. J Vasc Intery Neurol. 2014;7:23-5.
Ashcroft FM, Puljung MC, Vedovato N. Neonatal Diabetes and the KATP Channel: From Mutation to Therapy. Trends Endocrinol Metab. 2017;28:377-387.
Kazemi A, McLaren JW, Kopczynski CC, et al. The Effects of Netarsudil Ophthalmic Solution on Aqueous Humor Dynamics in a Randomized Study in Humans. J Ocul Pharmacol Ther. 2018;34:380-386.
Kwon YH. Fingert JH, Kuehn MG, Alward W.L. Primary open-angle glaucoma. N Engl J Med 2009;360:1113-1124.

(Continued)

*Primary Examiner* — Kortney L. Klinkel
*Assistant Examiner* — William Y Lee
(74) *Attorney, Agent, or Firm* — Umberg Zipser LLP

(57) ABSTRACT

Provided herein are methods of treating glaucoma in a patient, comprising: obtaining a biological sample from the patient; testing the biological sample for presence of a mutation in Kir6.2 protein or KCNJ11 gene; and provided that the biological sample tests positive for the presence of a mutation in Kir6.2 protein or KCNJ11 gene, administering to the patient a therapeutically effective amount of a composition comprising tolbutamide or a physiologically equivalent salt or solvate thereof and a pharmaceutically acceptable carrier. Also provided herein are methods of maintaining and/or improving eye health in a subject, comprising: administering to the patient a therapeutically effective amount of a composition comprising tolbutamide or a physiologically equivalent salt or solvate thereof, and a pharmaceutically acceptable carrier.

15 Claims, 4 Drawing Sheets

(56) References Cited

OTHER PUBLICATIONS

Fan N, Wang P, Tang L, Liu X. Ocular blood flow and normal tension glaucoma. Biomed Res Int. 2015; 2015:308505.
Thonginnetra O, Greenstein VC, Chu D, et al. Normal versus High Tension Glaucoma: A Comparison of Functional and Structural Defects, J Glaucoma 2010; 19: 151-157.
Chowdhury UR, Bahler CK, Hann CR, et al. ATP-Sensitive Potassium (K ATP) Channel Activation Decreases Intraocular Pressure in the Anterior Chamber of the Eye. Invest. Ophthalmol. Vis. Sci. 2011;52:6435-6442.
Chowdhury UR, Holman B, Fautsch MP. ATP-Sensitive Potassium (K(ATP)) Channel Openers Diazoxide and Nicorandil Lower Intraocular Pressure In Vivo. Invest. Ophthalmol. Vis. Sci. 2013;54:4892-4899.

* cited by examiner

Effect of 0.4% Tolbutamide on IOP of a Glaucoma Patient

METHODS AND COMPOSITIONS FOR IMPROVING EYE HEALTH

CROSS-REFERENCE TO RELATED APPLICATIONS

This application claims the benefit of priority to U.S. Provisional Patent Application Ser. No. 62/502,268 filed May 5, 2017, the entire contents of which is incorporated herein by reference.

FIELD OF THE INVENTION

The present disclosure relates to eye care products.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Aqueous humor is a transparent, watery fluid similar to plasma, which is secreted from the ciliary epithelium. It's made up of 99.9% water—the other 0.1% consists of sugars, vitamins, proteins and other nutrients. It fills both the anterior and the posterior chambers of the eye. This fluid nourishes the cornea and the lens, as well as giving the eye its shape.

The aqueous humor plays an essential role in the health of the eye. As well as nourishing the cornea and the lens by supplying nutrition such as amino acids and glucose, the aqueous humor maintains intraocular pressure, transports vitamin C in the front segment to act as an anti-oxidant agent, and provides inflation for expansion of the cornea, which in turn protects against dust, wind, pollen grains, and a number of pathogens. Thus, continuous production of aqueous humor is critical in ensuring that the optical physics and health of the eye are properly maintained.

Production of aqueous humor in the eye may be affected due to several reasons, such as, for example, glaucoma, cataract, old age, etc. Thus, there remains a need in the art for new compositions improving eye health by regulating the production of aqueous humor.

SUMMARY OF THE DISCLOSURE

Various embodiments disclosed herein include a method of treating glaucoma in a patient, comprising: obtaining a biological sample from the patient; testing the biological sample for presence of a mutation in Kir6.2 protein or KCNJ11 gene; and provided that the biological sample tests positive for the presence of a mutation in Kir6.2 protein or KCNJ11 gene, administering to the patient a composition comprising a therapeutically effective amount of tolbutamide or a physiologically equivalent salt or solvate thereof and a pharmaceutically acceptable carrier, and wherein tolbutamide is at a concentration of 0.1-0.9% (w/v). In one embodiment, the mutation is a nonsense mutation, rs5215, in the KCN11 gene, which is a loss of function mutation defined as a mutation that results in reduced or abolished protein function. In one embodiment, the mutation is a V337I mutation in Kir6.2 protein. In one embodiment, the mutation is a nonsense mutation, rs5219, in the KCN11 gene, which is a loss of function mutation defined as a mutation that results in reduced or abolished protein function. In one embodiment, the mutation is a E23K mutation in Kir6.2 protein. In one embodiment, the presence of a mutation is determined using a single nucleotide polymorphism (SNP) genotyping method. In one embodiment, the patient further has type 2 diabetes. In one embodiment, the pharmaceutically acceptable carrier is an ophthalmically acceptable carrier. In one embodiment, the dosages are administered from 1 to 4 times per day. In one embodiment, the method further comprises administration by topical application to the eye. In one embodiment, the method further comprises administration by injection into the anterior chamber of the eye. In one embodiment, the method further comprises administration using an ocular insert. In one embodiment, administration of the tolbutamide increases aqueous humor production by at least 150%. In one embodiment, administration of the tolbutamide increases aqueous outflow by at least 350%. In one embodiment, the glaucoma is normal tension open angle glaucoma or exfoliative glaucoma.

Various embodiments disclosed herein also include a method of diagnosing a disease in a subject, comprising: obtaining a biological sample from the subject; testing the biological sample for presence of a mutation in Kir6.2 protein or KCNJ11 gene; and diagnosing a disease in the subject if the biological sample tests positive for the presence of a mutation in Kir6.2 protein or KCNJ11 gene. In one embodiment, the disease is glaucoma.

In one embodiment, the disease is diabetes. In one embodiment, the mutation is a nonsense mutation, rs5215, in the KCN11 gene. In one embodiment, the mutation is a V337I mutation in Kir6.2 protein. In one embodiment, the mutation is a nonsense mutation, rs5219, in the KCN11 gene. In one embodiment, the mutation is a E23K mutation in Kir6.2 protein. In one embodiment, the method further comprises treating the disease by administering to the subject a composition comprising a therapeutically effective amount of tolbutamide or a physiologically equivalent salt or solvate thereof and a pharmaceutically acceptable carrier.

Embodiments of the present disclosure also include a method of maintaining and/or improving eye health in a subject, comprising: administering to the patient a composition comprising a therapeutically effective amount of tolbutamide or a physiologically equivalent salt or solvate thereof, and a pharmaceutically acceptable carrier, wherein tolbutamide is in the composition at a concentration of 0.1-0.9% (w/v). In one embodiment, the tolbutamide increases aqueous humor production by at least 150%. In one embodiment, the 0.4% tolbutamide increases aqueous outflow by at least 350%. In one embodiment, the pharmaceutically acceptable carrier is an ophthalmically acceptable carrier.

Embodiments of the present disclosure also include a method for regulating aqueous humor outflow via the ciliary body/trabecular meshwork/Schlemm's canal complex in an eye of a glaucoma patient, said method comprising: administering to the eye composition comprising a compound that specifically inhibits the Kir6.2 KATP channel.

Various embodiments disclosed herein further include a method of maintaining and/or improving eye health in a subject, comprising: administering to the eye of the subject a composition comprising a therapeutically effective amount of a compound that reestablishes the open/close probability requirements of the Kir6.2 KATP channel to normalize aqueous production/outflow dynamics.

Embodiments of the instant disclosure also include a method of treating ocular hypertension in a normal or glaucomatous subject, comprising: administering to the patient a therapeutically effective amount of a composition comprising tolbutamide, sulfonylurea, and/or glinide, or a physiologically equivalent salt or solvate thereof, and a pharmaceutically acceptable carrier. In one embodiment, the ocular hypertension is reduced by at least 20%. In one embodiment, the pharmaceutically acceptable carrier is an ophthalmically acceptable carrier.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
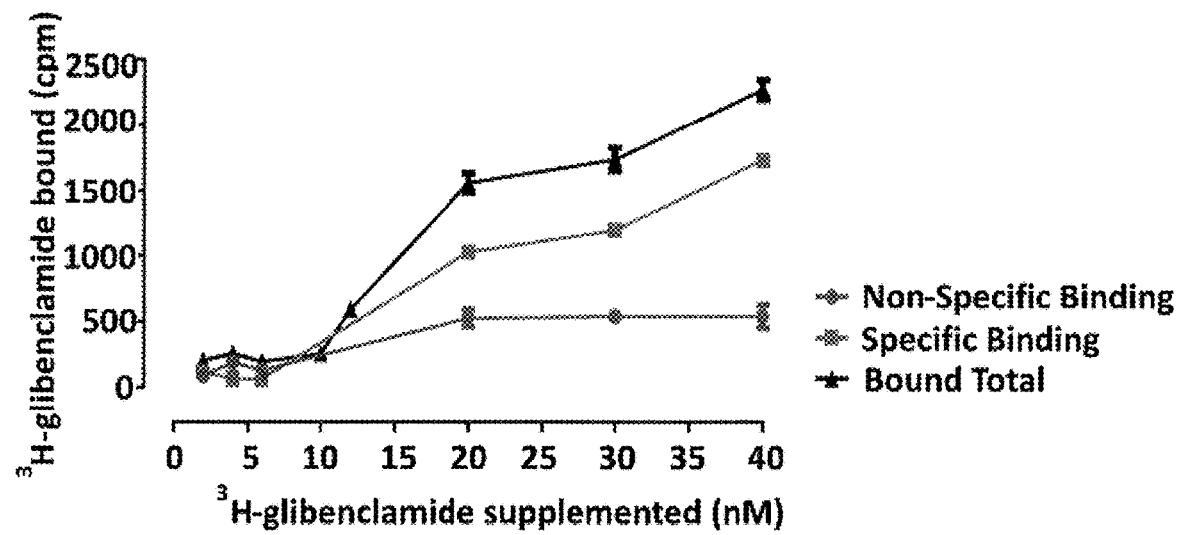
FIG. 1 depicts, in accordance with embodiments herein, binding of $^3$H-glibenclamide to bovine trabecular meshwork cells ($2.5 \times 10^5$ per 0.5 ml of reaction mixture) at various concentrations of ligand. Red: non-specific binding; green: specific binding. Shown is mean±SD.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the terms "ATP sensitive potassium channel," "ATP sensitive K+ channel," "KATP channel," or "$K_{ATP}$ channel" are used interchangeably and refer to a type of potassium channel that is gated by adenine nucleotides, typically being activated by falling ATP and rising ADP levels.

As used herein, the term "KATP channel activator" refers to a chemical compound that interacts with a KATP channel and (a) increases the baseline activity of the KATP channel or (b) increases cell membrane permeability to potassium ions.

As used herein, the term "KATP channel inhibitor" refers to a chemical compound that interacts with a KATP channel and (a) decreases the baseline activity of the KATP channel or (b) decreases cell membrane permeability to potassium ions.

As used herein, the term "subject" refers to a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal.

As used herein, the term "patient" refers to a subject afflicted with a disease, condition, or disorder. The term "patient" includes human and veterinary subjects. In some aspects of the disclosed methods, the subject has been diagnosed with a need for treatment of an eye disease including, but not limited to glaucoma, dry eyes, and/or cataract.

As used herein, the term "pharmaceutically acceptable carrier," refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

As used herein, the term "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

As disclosed herein, the inventors have developed compositions and methods for regulating the production of aqueous humor. In one embodiment, the production of aqueous humor is regulated by administering an inhibitor of the Kir6.2 KATP channel. In some embodiments, the composition is formulated with a pharmaceutically acceptable vehicle or excipient selected from the group comprising of ophthalmically acceptable preservatives, surfactants, viscosity enhancers, penetration enhancers, gelling agents, hydrophobic bases, vehicles, buffers, sodium chloride, and water.

Various embodiments disclosed herein include an anti-aging composition for maintaining and/or improving eye health in a subject, comprising: administering to the eye of the subject a therapeutically effective amount of a compound that modulates the ATP-sensitive potassium (KATP) channel, specifically the channel isoform comprising four SUR2A/B or SUR1 and four Kir6.2 subunits, which he inventors have discovered to have a loss of function mutation in glaucoma patients, and a pharmaceutically acceptable carrier. In one embodiment, the compound increases outflow of aqueous humor. The inventors have shown that a mutation in the KCNJ11 gene (rs5215) of the KATP channel substitutes isoleucine for valine at position 337 (V337I) of the Kir6.2 protein. The isoleucine for valine substitution has been shown to result in loss of function, which has been linked to sudden infant death when occurs in Kir6.1 (Tester D J, et al. 2011. Loss-of-function mutations in the KCNJ8-encoded Kir6.1 KATP channel and sudden infant death syndrome. (Circ Cardiovase Genet 4:510-515). Since KATP channels are modulated by intracellular levels of ATP, i.e. ATP inhibits (closes) and ADP stimulates (open) KATP channels, the ATP:ADP ratio is a major factor determining channel activity. As disclosed herein the loss of function the inventors have shown in trabecular meshwork from human donors implies that inhibition of the KATP channels required a higher than normal concentration of ATP; however, with age metabolism slows and less ATP is produced resulting in the trabecular meshwork KATP channels being in the open state for longer periods of time, reducing aqueous outflow and increasing IOP, which is a major risk for glaucoma. Drugs that inhibit the KATP channel restore the normal open/closed probability state of the channel to establish the aqueous humor outflow that is present in normal, non-glaucomatous individuals. In one embodiment, the compound is an inhibitor of the Kir6.2 KATP channel. In one embodiment, the compound is a glinide. In one embodiment, the compound is a sulfonylurea. In one embodiment, the compound is selected from the group consisting of carbutamide, acetohexamide, chlorpropamide, tolbutamide, glipizide, gliclazide, glibenclamide, glyburide, glibornuride, gliquidone, glisoxepide, glyclopyramide, glimepiride, chlorpromazine, 2,3-butanedione and hydroxydecanoic acid, or a physiologically acceptable salt or solvate thereof. In one embodiment, the pharmaceutically acceptable carrier is an ophthalmically acceptable carrier. In one embodiment, the compound is administered in an amount between about 0.1 µg and about 10 mg. In one embodiment, the dosages are administered from 1 to 4 times per day. In one embodiment, the compound is administered by topical application to the eye. In one embodiment, the compound is administered by injection into the anterior chamber of the eye. In one embodiment, the compound is administered using an ocular insert. In one embodiment, the subject is a mammal. In one embodiment, the subject is a human. In one embodiment, the subject is a glaucoma patient. In one embodiment, the glaucoma is normal tension open angle glaucoma. In one embodiment, the glaucoma is high tension open angle glaucoma. In one embodiment, the glaucoma is exfoliative angle glaucoma. In one embodiment, the subject is a cataract patient. In one embodiment, the composition is administered after cataract surgery.

In one embodiment, disclosed herein is a method of treating glaucoma in a patient, comprising: obtaining a biological sample from the patient; testing the biological sample for presence of a mutation in Kir6.2 protein or KCNJ11 gene; and provided that the biological sample tests positive for the presence of a mutation in Kir6.2 protein or KCNJ11 gene, administering to the patient a composition comprising a therapeutically effective amount of tolbutamide or a physiologically equivalent salt or solvate thereof and a pharmaceutically acceptable carrier. In one embodiment, the tolbutamide is in a suspension or solution at a concentration of 0.1-0.2%, 0.2-0.3%, 0.3-0.4%, 0.4-0.5%, 0.5-0.6%, 0.6-0.7%, 0.7-0.8% (w/v). In one preferred embodiment, the tolbutamide is in a suspension or solution at a concentration of 0.4% (w/v). In one embodiment, the mutation is a nonsense mutation, rs5215, in the KCN11 gene. In one embodiment, the mutation is a V337I mutation in Kir6.2 protein. In one embodiment, the mutation is a nonsense mutation, rs5219, in the KCN11 gene. In one embodiment, the mutation is a E23K mutation in Kir6.2 protein. In one embodiment, the patient further has type 2 diabetes. In one embodiment, the pharmaceutically acceptable carrier is an ophthalmically acceptable carrier. In one embodiment, the dosages are administered from 1 to 4 times per day. In one embodiment, the method further comprises administration by topical application to the eye. In one embodiment, the method further comprises administration by injection into the anterior chamber of the eye. In one embodiment, the method further comprises administration using an ocular insert. In one embodiment, administration of the tolbutamide increases aqueous humor production by at least 100%, or more preferably at least 110%, or more preferably at least 120%, or more preferably at least 130%, or more preferably at least 140%, or most preferably at least 150%. In one embodiment, administration of the tolbutamide increases aqueous outflow by at least 150%, or more preferably at least 200%, or more preferably at least 250%, or more preferably at least 275%, or more preferably at least 300%, or more preferably at least 325%, or most preferably at least 350%. In one embodiment, the glaucoma is normal tension open angle glaucoma or exfoliative angle glaucoma.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the present disclosure can also contain any pharmaceutically acceptable carrier.

The pharmaceutical compositions according to the present disclosure can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the present disclosure may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21st edition, Williams & Wilkins PA, USA) (2005).

Typical dosages of an effective composition can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

In one embodiment, disclosed herein is a method of diagnosing a disease in a subject, comprising: obtaining a biological sample from the subject; testing the biological sample for presence of a mutation in Kir6.2 protein or KCNJ11 gene; and diagnosing a disease in the subject if the biological sample tests positive for the presence of a mutation in Kir6.2 protein or KCNJ11 gene. In one embodiment, the disease is glaucoma. In one embodiment, the disease is diabetes. In one embodiment, the mutation is a nonsense mutation, rs5215, in the KCN11 gene. In one embodiment, the mutation is a V337I mutation in Kir6.2 protein. In one embodiment, the mutation is a nonsense mutation, rs5219, in the KCN11 gene. In one embodiment, the mutation is a E23K mutation in Kir6.2 protein. In one embodiment, the method further comprises treating the disease by administering to the subject a composition comprising a therapeutically effective amount of tolbutamide or a physiologically equivalent salt or solvate thereof and a pharmaceutically acceptable carrier.

In one embodiment, disclosed herein is a method of maintaining and/or improving eye health in a subject, comprising: administering to the eye of the subject a composition comprising a therapeutically effective amount of a compound that modulates the Kir6.2 KATP channel and a pharmaceutically acceptable carrier. In one embodiment, the compound increases outflow of aqueous humor. In one embodiment, the compound is an inhibitor of the Kir6.2 KATP channel. In one embodiment, the compound is a sulfonylurea. In one embodiment, the compound is selected from the group consisting of carbutamide, acetohexamide, chlorpropamide, tolbutamide, glipizide, gliclazide, glibenclamide, glyburide, glibornuride, gliquidone, glisoxepide, glyclopyramide, glimepiride, chlorpromazine, 2,3-butanedione and hydroxydecanoic acid, or a physiologically acceptable salt or solvate thereof. In one embodiment, the pharmaceutically acceptable carrier is an ophthalmically acceptable carrier. In one embodiment, the compound is administered in an amount between about 0.1 µg and about 10 mg. In one embodiment, the dosages are administered from 1 to 4 times per day. In one embodiment, the compound is administered by topical application to the eye. In one embodiment, the compound is administered by injection into the anterior chamber of the eye. In one embodiment, the compound is administered using an ocular insert. In one embodiment, the subject is a glaucoma patient. In one embodiment, the glaucoma is normal tension open angle glaucoma. In one embodiment, the glaucoma is high tension open angle glaucoma. In one embodiment, the glaucoma is exfoliative angle glaucoma. In one embodiment, the subject is a cataract patient. In one embodiment, the composition is administered after cataract surgery.

In one embodiment, disclosed herein is a method for regulating aqueous humor outflow via the ciliary body/ trabecular meshwork/Schlemm's canal complex in an eye of a glaucoma patient, said method comprising: administering to the eye a compound that specifically modulates the Kir6.2 KATP channel. In one embodiment, the regulation of aqueous humor outflow is an increase in aqueous humor outflow. In one embodiment, the compound is an inhibitor of the Kir6.2 KATP channel. In one embodiment, the compound is present in an ophthalmically acceptable carrier in an amount effective to increase aqueous outflow. In one embodiment, the compound is administered in a dosage between about 0.1 µg and about 10 mg of the compound. In one embodiment, the compound is administered between 1 and 4 times per day. In one embodiment, the method further comprises administration by topical application to the eye. In one embodiment, the method further comprises administration by injection into the anterior chamber of the eye. In one embodiment, the method further comprises administration using an ocular insert. In one embodiment, the Kir6.2 KATP channel inhibitor is used to increase aqueous humor outflow resulting in lower intraocular pressure in high tension open angle glaucoma. In one embodiment, the Kir6.2 KATP channel inhibitor is used to increase aqueous humor outflow in normal tension open angle glaucoma. In one embodiment, the Kir6.2 KATP channel inhibitor is used to increase aqueous humor outflow in exfoliative angle glaucoma. In one embodiment, the Kir6.2 KATP channel inhibitor is used to increase aqueous humor outflow resulting in lower IOP after cataract surgery. In one embodiment, the compound is a sulfonylurea. In one embodiment, the compound is selected from the group consisting of carbutamide, acetohexamide, chlorpropamide, tolbutamide, glipizide, gliclazide, glibenclamide, glyburide, glibornuride, gliquidone, glisoxepide, glyclopyramide, glimepiride, chlorpromazine, 2,3-butanedione and hydroxydecanoic acid, and therapeutically equivalent salts and derivatives thereof.

Embodiments of the present disclosure are further described in the following examples. The examples are merely illustrative and do not in any way limit the scope of the invention as claimed.

EXAMPLES

Example 1

Glaucoma

Glaucoma is the second leading cause of irreversible blindness worldwide, and it is expected that 80 million people will suffer from this disease by the year 2020 [Quigley H A, Broman A T, 2006. Br J Ophthalmol. 90: 262-267]. The glaucomas are classified as open-angle (open iridocorneal angle), closed-angle (closed iridocorneal angle), and developmental glaucomas. Glaucomas are divided into primary and secondary types. Secondary glaucomas are diseases secondary to another condition, such as exfoliation or pigment-dispersion syndrome, whereas primary glaucomas are diseases in which aqueous outflow is diminished. Primary open-angle glaucoma includes both adult-onset disease (occurring after 40 years of age) and juvenile-onset disease (occurring between the ages of 3 and 40 years of age). Primary open angle glaucoma (POAG) is the most common form of glaucoma and is associated with the progressive loss of retinal ganglion cell axons, along with supporting glia and vasculature. Increased intraocular pressure (IOP) is present in 60-70% of patients with POAG, referred to as high tension glaucoma (HTG), whereas 30-40% of patients with POAG have IOP within normal limits, referred to as normal tension glaucoma (NTG).

The pathology shared by the heterogeneous group of glaucoma disorders is characterized by progressive optic nerve atrophy and retinal ganglion cell (RGC) death [Vohra R, Tsai J C, Kolko M, 2013. The role of inflammation in the pathogenesis of glaucoma. Surv Ophthalmol 58:311-320], which gradually lead to visual field loss. Although the research in the field of glaucoma is substantial, the pathological mechanisms involved in the onset and development of the disease are still not completely understood. Neuronal degeneration in glaucoma might be due to a combination of molecular factors, such as compromised retrograde axonal transport along the optic nerve, neurotrophin deprivation, increased oxidative stress, or excitotoxic stress caused by a glutamate impaired response [Madeira M H, Boia R, et al. 2015. Contribution of microglia-mediated neuroinflammation to retinal degenerative diseases. Mediators Inflamm. 2015:15; Almasieh M, Wilson A M, et al. 2012. The molecular basis of retinal ganglion cell death in glaucoma. Prog Retin Eye Res. 31:152-181].

Advanced age and elevated intraocular pressure (IOP) are the main risk factors for the onset and progression of glaucoma. Nevertheless, 30-40% of patients with glaucoma present IOP values within the normal range [Sommer A et al. 1991. Relationship Between Intraocular Pressure and Primary Open Angle Glaucoma Among White and Black Americans: The Baltimore Eye Survey. Arch Ophthalmol 109:1090-1095; Fan N, Wang P, et al. 2015. Ocular blood flow and normal tension glaucoma. Biomed Res Int. 2015: 308505]; of particular note is the fact that glaucoma patients with normal IOP (normal tension glaucoma, NTG) appear to have more localized and central visual field defects than high tension glaucoma (HTG) patients [Thonginnetra O, Greenstein V C, Chu D, et al., 2010. Normal versus High Tension Glaucoma: A Comparison of Functional and Structural Defects, J Glaucoma; 19: 151-157] suggesting that increased IOP is not essential for neuronal degeneration. Since elevated IOP is the only modifiable risk factor, therapeutic strategies target lowering of the IOP and include pharmacological treatments, surgical procedures, and laser treatment. Although high intraocular IOP is considered as the most important risk factor for the development of glaucoma, it is neither necessary nor sufficient since in many patients RGC loss continues in spite of IOP [Edward Brubaker R F. Delayed functional loss in glaucoma. LII Jackson Memorial Lecture. 1996. Am J Ophthalmol. 121: 473-483]; in fact, the risk of unilateral blindness in patients with treated open-angle glaucoma is estimated to be around 27% [Hattenhauer M G, Johnson D H, et al. 1998. The probability of blindness from open-angle glaucoma. Ophthalmology. 105:2099-2104.]

The fact that aqueous humor outflow is diminished significantly in glaucoma may engender a harmful environment in the eye and possibly in other neural structures, leading to altered metabolism and retinal ganglion cell degeneration. Recent research points to structural, metabolic and functional glaucoma-driven changes in both the eye and the brain [Murphy M C, Conner P I, Teng C Y, et al. 2016. Retinal Structures and Visual Cortex Activity are Impaired Prior to Clinical Vision Loss in Glaucoma. Sci Rep. 6: 31464], and it appears that glaucoma deterioration is already present in the eye and the brain before substantial vision loss can be detected clinically in patients [Wollstein G. et al. 2012. Retinal nerve fibre layer and visual function loss in glaucoma: the tipping point. Br J Ophthalmol 96, 47-52; Alasil T. et al. 2014. Correlation of retinal nerve fiber layer thickness and visual fields in glaucoma: a broken stick model. American journal of ophthalmology 157, 953-959]. Some of the metabolic changes in glaucoma that may underlay its pathology are calcium disregulation [He Y, Ge, Tombran-Tink J, 2008. Mitochondrial Defects and Dysfunction in Calcium Regulation in Glaucomatous Trabecular Meshwork Cells. Investigative Ophthalmology & Visual Science. 49: 4912-4922], alterations in glutamate and glutamine [Hu R G, et al. 2012. Alterations of glutamate, glutamine, and related amino acids in the anterior eye secondary to ischaemia and reperfusion. Curr Eye Res. 37:633-43]

Even though glaucoma is a defect in aqueous outflow, which may or may not result in increased IOP, reduction of IOP for both high tension and normal tension glaucoma is currently the only dependable pharmaceutical approach to the management of POAG. Therapeutic agents for POAG treatment include prostaglandin analogs, β-adrenergic receptor blockers, αβ-adrenergic receptor blockers, a1-adrenergic receptor blockers, α2-adrenergic receptor agonist, and carbonic anhydrase inhibitors (Kwon et al., 2009, N Engl J Med 360:1113-1124; Abu-Amero, et al., 2015, IJMS 16:28886-2891; Sommer A et al, 1991, Arch Ophthalmol 109:1090-1095)

Topical prostaglandin analogs (PAs) are the most frequently drugs to treat glaucoma. Used once a day PAs lower IOP by 25-30% and stabilize it at a lower level by increasing uveoscleral outflow. PAs can have significant side-effects, such as conjunctival hyperemia, irreversible darkening of the iris in people with multicolor irises, increased periorbital (eyelid) skin pigmentation, local irritation, itching, dry eye, blurred vision, periorbital fat atrophy, and in rare cases may cause uveitis or cystoid macular edema. Beta blockers lower IOP by 20-25% with once- or twice-daily dosing by decreasing aqueous formation. Beta blockers are well tolerated topically and rarely cause local adverse effects, such as stinging, itching, redness and blurred vision. Beta blockers, however, even though administered locally to the eye can have significant systemic side effects including dizziness, bradycardia, respiratory depression, masking of hypoglycemia, and interfering with the treatment of asthma by beta2-agonists. The systemic side effects have limited their use as first-line therapy. Carbonic anhydrase inhibitors (CAIs), like beta blockers, decrease IOP by decreasing production of aqueous humor. CAIs are very effective and decrease IOP by 30-50%, but have many systemic adverse effects, which restrict their use. When any one drug does not lower the IOP to a safe level, a combination of 2 or more drugs are used to achieve the desired IOP; however, the side effects of drug combination are also additive. When pharmacological agents are no longer effective at lowering IOP sufficiently, surgical intervention is necessary in the form of laser trabeculoplasty or implantation of devices to allow outflow of aqueous humor.

It should also be noted that even when drugs are effective at lowering IOP, retinal ganglion cells (RGCs) continue to undergo apoptosis and consequent vision loss progresses, albeit at lower rate. Current drugs for glaucoma affect either aqueous humor production or the nonconventional uveoscleral outflow pathway. There are no drugs available that increase aqueous humor outflow via the conventional trabecular meshwork/Schlemm's canal pathway. Therefore, it would be desirable to provide drugs useful for the control of intraocular pressure, particularly for the treatment of glaucoma and other disorders related to elevated intraocular pressure, where such drugs increase aqueous humor via the conventional trabecular meshwork/Schlemm's canal pathway and have fewer side effects when compared to present drugs. Drugs for the treatment of elevated IOP due to other conditions, such as surgical intervention for cataracts would also be desirable. Such drugs should be safe, non-toxic, and be amenable to incorporation in carriers and vehicles suitable for administration to the eye, either topically, by injection, or by ocular insert. These and other objectives will be met by the methods and compositions of the present invention, as described in more detail hereinafter.

Example 2

KATP Channel

The ATP-sensitive K+ (KATP) channel was first described by Noma (Noma A, 1983, Nature, 305:147) in cardiac muscle and has since been identified in a number of cells and tissues (Meisheri K, et al, 1995, Molecular Pharmacology 47:155; Schmid-Antomarchi H et al, 1987, Biophysical Research Communications 146:21; Spruce A, et al., 1987, Journal of Physiology 382:213; Niki I, Ashcroft S J, 1993, Neuropharmacology 32:9510). KATP channels couple cell metabolism to electrical activity and thus regulate cell functionality, such as insulin secretion from pancreatic β-cells, transmitter release from brain neurons, and regulate the cellular and extracellular water balance.

The KATP channels, members of the inward rectifying K+ channel family, are octameric complexes composed of four Kir6.x subunits and four sulfonylurea receptors (SUR) subunits (Shyng S, Nichols C, 1997, J Gen Physiol 110:655). The Kir6 subfamily is a member of the inward rectifier family and has two members, Kir6.1 and Kir6.2. SURs are members of the ABC superfamily and comprise sulfonyl urea receptors SUR 1, SUR 2A and SUR 2B (Bryan J et al., 2007, Pflugers Arch—Eur J Physiol 453:703; Aittoniemi J et al., 2009, Philosophical Transactions of the Royal Society B: Biological Sciences 364:257). SURs, by themselves, perform no recognized function. Instead, they undergo association with heterologous pore-forming subunits to form ion channels, which they regulate. SURs contains two nucleotide-binding domains as well as low and high affinity binding sites for sulfonylurea drugs and related compounds, such as glibenclamide and tolbutamide, which are potent inhibitors of SUR-regulated channel activity. SURs are the target of sulfonylurea and glinide drugs used to treat diabetes mellitus type 2, neonatal diabetes, and some forms of congenital hyperinsulinemia. In the pancreatic β-cells, binding of sulfonylureas and glinides to KATP channels induces channel closure, causing membrane depolarization, which activates voltage-dependent $Ca^{2+}$ channels in the β-cell plasma membrane and the resulting Ca2+ influx triggers $Ca^{2+}$-dependent insulin granule exocytosis (Ashcroft F, Rorsman P, 1989, Prog. Biophys. Malec. Biol, 54:87; Proles P, et al., 2002, Diabetes 51:5368).

KATP channel activity is thought to be regulated mainly by the metabolic activity of the cell via changes in the concentrations of intracellular adenine nucleotides. Electrophysiological studies have suggested that, based on their kinetics and pharmacological properties, distinct types of KATP channels can be detected in various tissues. These different types of KATP channels appear to result from cell-specific expression and the combination of different subunits. Indeed, two Kir6.x (Kir6.1, also known as KCNJ8, and Kir6.2, also known as KCNJ11) and two SURx (SUR1, also known as ABCC8, and SUR2, also known as ABCC9) subunits have been identified, and their various combinations can give rise to functional KATP channel subtypes (Seino S, Miki T, 2003 Progress in Biophysics and Molecular Biology 81:133). Six functional KATP channels have been identified, specifically SUR1/KIR6.1, SUR1/KIR6.2, SUR2B/KIR6.1, SUR2A/Kir6.1, SUR2A/KIR6.2, and SUR2B/KIR6.2. These channels have different sensitivities to ATP, channel openers and channel inhibitors as well as tissue distribution.

The KATP channels are regulated by intracellular ATP such that it is spontaneously active in the absence of ATP and closed by increasing ATP concentration in the cytoplasmic side of the membrane. The KATP channels are not activated by intracellular Ca+2, and gating of the channel is independent of membrane potential. The channel is selective for K+, and it is selectively inhibited by sulfonylurea compounds and glinides. All pharmacological sulfonylureas contain a central S-arylsulfonylurea structure with a p-substituent on the phenyl ring (R) and various groups terminating the urea N' end group (R2). As an example for chlorpropamide the p-substituent (R) on the phenyl ring is chloride (Cl—) and the substituent at the N' of urea (R2) is a propyl group. Pharmacological sulfonylureas include carbutamide, acetohexamide, chlorpropamide, and tolbutamide. gliclazide, glibenclamide, glyburide, glibornuride, gliquidone, glisoxepide, and glyclopyramide, glimepiride. A number of other sulfonylureas are used as biopesticides because they can interfere with plant biosynthesis of the amino acids valine, isoleucine, and leucine. Glinides are a heterogeneous class of insulin secretion stimulating agents that bind to the KATP channel and close the channel Glinides bind to the sulfonylurea receptor with a lower affinity than sulfonylureas (Stephan D, Winkler M, Kühner P, Russ U, Quast U. Selectivity of repaglinide and glibenclamide for the pancreatic over the cardiovascular KATP Channels. Diabetologia 2006; 49:2039-2048)

Sulfonylureas and glinides, which target KATP channels, are a mainstay of diabetes therapy. KATP channels are hetero-octameric structures composed of four regulatory sulfonylurea receptor subunits (SURs) and four Kir6.x subunits, the latter forming a central ion pore that permits K+ efflux. The importance of SUR1 as a regulator of KATP channel activity is exemplified by the fact that loss- and gain-of-function mutations result in congenital hyperinsulinemia (HI) and neonatal diabetes, respectively. KATP channels play a key role in insulin secretion both in response to glucose, the main physiological stimulus, and to sulfonylurea drugs that are used to treat type 2 diabetes. Loss-of-function mutations reduce KATP channel activity, producing a persistent membrane depolarization that leads to the activation of voltage-gated $Ca^{2+}$ influx and continuous insulin secretion, irrespective of the blood glucose level. Conversely, gain-of-function mutations prevent the channel from closing in response to metabolically generated changes in adenine nucleotides. Thus the β-cell remains hyperpolarized even when blood glucose levels rise, thereby keeping voltage-gated $Ca^{2+}$ channels closed and preventing $Ca^{2+}$ influx and insulin secretion. Congenital HI is characterized by abnormal high levels of insulin secretion despite severe hypoglycemia. A number of mutations in Kir6.2 have been identified in familial early-onset type 2 diabetic probands and their families. Of particular interest is that increased risk of glaucoma is associated with diabetes duration, and fasting glucose levels.

To investigate the effect of modulators of openers and blockers of the KATP channel in higher animals, the inventors tested the effect on cynomologous monkeys; short-term, 1-hour studies in monkeys showed that blockers of the KATP channel decreased IOP and openers elevated IOP. Since blockers of the KATP channel are drugs that have been used for over 50 years to treat diabetes, the inventors obtained ethical board permission to treat glaucoma patients with a tolbutamide solution at a concentration 500 times lower that the dose used to treat diabetes. Tolbutamide, a well-known and world-wide clinically approved drug to treat Type II diabetes, was used as the prototype blocker of the KATP channel. It was unexpected that 1 drop of tolbutamide twice daily decreased IOP for the 6 days of the study. Tolbutamide solution decreased IOP not only in glaucomatous patients, but also in patients with elevated IOP after cataract surgery. More surprisingly and unexpected was the result that after 3 days, administration of one drop of 0.4% tolbutamide solution to the eye twice daily increased aqueous formation by approximately 150% and increased outflow via the trabecular meshwork/Schlemm's canal by 350%. These data, in conjunction with data showing that tolbutamide administered topically to the eye twice daily decreased IOP in 5 patients suffering with glaucoma and one patients with elevated IOP after cataract surgery, clearly indicated that in humans, blockers and not openers of the KATP channel increase aqueous outflow and can decrease IOP.

Example 3

Glaucoma Treatment

Since current drugs to treat glaucomas and elevated IOP slow but do not prevent RGCs degeneration and do not increase sufficiently aqueous humor outflow via the ciliary body/trabecular meshwork/Schlemm's canal complex, its natural outflow pathway, and in addition have significant side effects, there is an urgent need for novel useful drugs for the treatment of glaucomas and elevated IOP by regulating aqueous humor dynamics via the ciliary body/trabecular meshwork/Schlemm's canal pathway. Novel methods and compositions for treating glaucomas and intraocular pressure in the eye of a patient are presented in this disclosure. The compositions comprise compounds that bind to the sulfonylurea receptors moiety of the KATP channels closing the channels (channel blocker) and thus modulate cellular potassium efflux, increase outflow facility via the ciliary body/trabecular meshwork/Schlemm's canal complex, and decrease IOP. The KATP-channel blockers compounds are preferably sulfonylurea compounds, more preferably being elected from the group that include carbutamide, acetohexamide, chlorpropamide, and tolbutamide, gliclazide, glibenclamide, glyburide (also known as Micronase), glibornuride, gliquidone, glisoxepide, and glyclopyramide, glimepiride (also known as Amaryland or Glimiprime), and therapeutically equivalent salts and derivatives thereof, and are preferably present in the compositions in concentrations from about 0.001% to10% by weight. Non-sulfonyl urea compounds, however, have also been found to be effective, such chlorpromazine, 2,3-butanedione and hydroxydecanoic acid.

Such compounds are delivered to the eye in an ophthalmically acceptable carrier in an amount effective to increase aqueous humor outflow whether exhibiting elevated IOP or normal IOP (normotensive glaucoma) and lower IOP when administered to an eye having elevated intraocular pressure. Suitable administration methods include, but are not limited to topical application, injection, and timed release using an ocular insert or equivalent formulation.

Example 4

Formulations

The methods and compositions of the present disclosure are intended for treatment of impaired aqueous humor outflow. In some embodiments, the impaired aqueous humor outflow is caused by glaucoma or other eye conditions. In some instances, the patient requiring treatment for impaired aqueous humor outflow may also manifest IOP elevation in the eye. The patient may be human, or other mammals.

Glaucoma is a term which embraces a group of ocular diseases characterized by normal aqueous humor production by the ciliary body and impaired aqueous humor outflow by the trabecular meshwork/Schlemm's canal pathway. The impaired aqueous outflow may result in hypoxic stress, oxidative stress, elevated levels of excitatory amino acids, such as glutamate and aspartate, decreased neurotrophic factors, and in about 60% of patients impaired aqueous outflow increases IOP. These consequences of decreased outflow result in damage and eventual death of retinal ganglion neurons, which is glaucoma. Glaucomas are well-described in the medical literature. In addition to glaucoma, other conditions in which disregulation of aqueous outflow results in elevated intraocular pressure levels include cataract surgery, steroid treatment, and treatment with other drugs known to elevate intraocular pressure. The methods and compositions of the present invention are intended to treat all such conditions, and are not limited to glaucoma or dry eyes only, in order to lower the intraocular pressure to avoid damage to the optic nerve and retinal ganglion cells.

It is expected that other selective KATP channel inhibitors will be identified in the future and that they will be useful in the methods of the present disclosure. KATP channels have been identified in many cell types, e.g., cardiac cells, skeletal and smooth muscle, neurons and pancreatic β-cells. It is very likely that KATP channels are found in many cells, and the data present in the Experimental section hereinafter indicate the presence of such an KATP channel in the trabecular meshwork cells of the eye. The inventors have shown that sulfonylurea compounds bind to a receptor present in trabecular meshwork cells and the kinetics of binding are the same as the binding of sulfonylurea compounds to pancreatic β-cells. In addition, glybenclamide (a sulfonylurea) and chlorpromazine inhibit potassium efflux from trabecular meshwork cells as indicated by $^{86}$Rubidiun efflux.

The KATP channel inhibiting compounds will be administered to the eye in amounts and over a schedule effective to lower the intraocular pressure of the eye, when the intraocular pressure is elevated or when it is necessary to lower the intraocular pressure to prevent damage to the optic nerve or when it is necessary to increase the outflow facility of the aqueous humor. The amount of the compound required for such lowering will depend on a number of factors, including degree of initial pressure elevation, condition of the patient, specific formulation, activity of the particular compound which is being administered, and the like, with exemplary amounts being in the range from about 50 μg to 5 mg per dose (i.e., single application of the composition), usually being from 250 μg to 1 mg per dose.

Topical compositions for delivering the KATP channel modulating compounds of the present invention will typically comprise the compound present in a suitable ophthalmically acceptable carrier, including both organic and inorganic carriers. Exemplary ophthalmically acceptable carriers include water, buffered aqueous solutions, isotonic mixtures of water and water-immiscible solvents, such as alkanols, aryl alkanols, vegetable oils, polyalkalene glycols, petroleum-based gels, ethyl-cellulose, carboxymethylcellulose, polyvinylpyrrolidones, isopropyl myristates, dextran, glycerin, dextran, hypromellose, polyethylene glycol, polysorbate, polyvinyl alcohol, povidone, or propylene glycol, and the like. Suitable buffers include sodium chloride, sodium borate, sodium acetate, gluconates, phosphates, and the like.

The formulations of the present disclosure may also contain ophthalmically acceptable auxiliary components, such as emulsifiers, preservatives, wetting agents, thixotropic agents (e.g., polyethylene glycols, antimicrobials, chelating agents, and the like). Particularly suitable antimicrobial agents include quaternary ammonium compounds, benzalkonium chloride, phenylmercuric salts, thimerosal, methylparaben, propyl paraben, benzyl alcohol, phenylethanol, sorbitan, monolaurate, triethanolamine, oleate, polyoxyethlene sorbitan monopalmitylate, dioctyl sodiumsulfosuccinate, monothioglycerol, and the like. Ethylenediamine tetracetic acid (EDTA) is a suitable chelating agent.

The following formulations are exemplary of the compositions of this disclosure. These formulations are illustrative only and are not intended to limit the scope of this invention and should not be so construed.

Formula 1.

| Component | Amount |
| --- | --- |
| Tolbutamide | 10 μg to 20 mg |
| Thimerosal | 0.001% |
| Phosphate Buffered Saline | 1 ml |

Formula 2

| Component | Amount |
| --- | --- |
| Tolbutamide | 10 μg to 20 mg |
| Hypromellose | 0.4% |
| Sodium Chloride to | 300 mOSm |
| Hydrochloric acid/sodium hydroxide | pH 6.7 |
| Thimerosal | 0.001% |

Formula 3

| Component | Amount |
| --- | --- |
| Glybenclamide | 1 μg to 20 mg |
| Sodium chloride | 8 mg |
| Boric acid | 1 mg |
| Benzalkonium chloride | 0.1 mg |
| Hydrochloric acid/sodium hydroxide | pH 7.0 |
| Water for injection (qs) | 1 ml |

Formula 4

| Component | Amount |
| --- | --- |
| Glybenclamide | 1 μg to 20 mg |
| Methyl paraben | 1 mg |
| Propyl paraben | 1 mg |
| Sodium chloride | 5 mg |
| Water for injection (qs) | 1 ml |

Example 5

Experimental Results

Effect of Tolbutamide on IOP of Normal Cynomologus Monkeys: Formulations of the KA channel inhibitor tolbutamidewere tested as a suspension and as a solution for its ability to lower intraocular pressure in normal cynomologus monkeys. For the suspension, 0.4% tolbutamide was prepared in NaCl/borate buffer (0.8 mg NaCl, 1.0 mg boric acid, pH 7.2, water to 1 ml; for the solution, 0.4% tolbutamide was solubilized in 0.25 M NaOH and added to 0.4% hypromellose (HPMC) and the pH adjusted to 6.7. Tonicity was adjusted to 300 mOSm with NaCl and preserved with 0.001% thimerosal. He suspension and solution were tested as follows: Monkeys were anesthetized with ketamine hydrochloride and the baseline IOP determined. One drop of drug was administered to the right eye and the IOP determined 1 hour later, while the animals were still under anesthesia; the left eye served as a control. Two animals for each treatment were used. The results are presented in Table 1. The decrease in IOP in the untreated eye is the result of anesthesia.

TABLE 1

| | | IOP mmHg (% Change) | | |
|---|---|---|---|---|
| | | pre-treatment | | 1 hour post-treatment |
| Treatment | | OD | OS | OD(treated) | OS (untreated) |
| Tolbutamide 0.4% | 1 | 24 | 24 | 15 (−37) | 18 (−25) |
| suspension | 2 | 24 | 22 | 18 (−25) | 19 (−14) |
| Tolbutamide 0.4% | 1 | 26 | 26 | 22 (−19) | 23 (−12) |
| solution | 2 | 22 | 23 | 17 (−23) | 17 (−26) |

The Presence of KATP in Trabecular Meshwork Cells: Aliquots of bovine trabecular meshwork were incubated on ice with various nM concentrations of $^3$H-glibenclamide. Non-specific binding was determined as the residual binding in the presence of 20 µM non-labeled glibenclamide. After 2 hrs incubation, $^3$H-bound glibenclamide was separated from free $^3$H-glibenclamide on Whatman GF/F filters soaked in incubation buffer. Specific binding as calculated as the difference between binding in the absence and presence of non-labeled 20 nM glibenclamide (FIG. 1). The data presented in FIG. 1 shows that trabecular meshwork cells have a receptor for glybenclamide and by analogy these cells have a receptor for other sulfonylureas.

Figure 2:
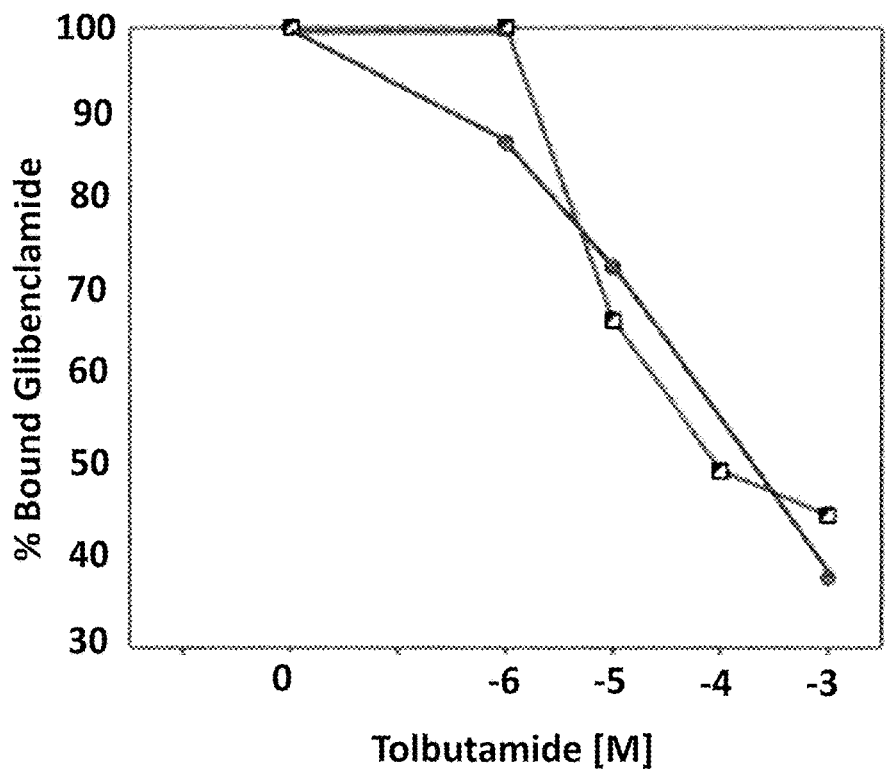
FIG. 2 depicts, in accordance with embodiments herein, displacement of $^3$H-glibenclamide bound to trabecular meshwork cells (green) and RIN-m5F cells (red) by tolbutamide.
Figure 3:
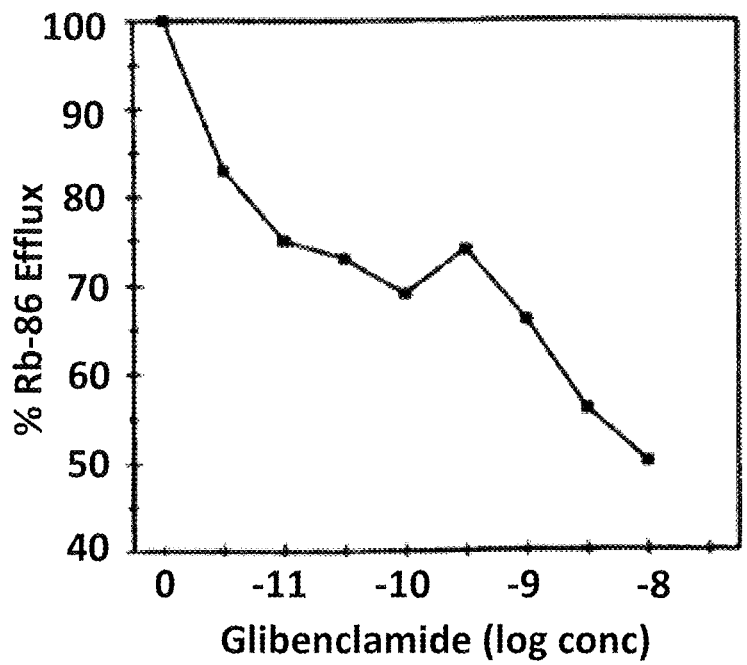
FIG. 3 depicts, in accordance with embodiments herein, effect of glybenclamide on the efflux of $^{86}$Rb from human trabecular meshwork cell. Glybenclamide inhibits $^{86}$Rb efflux in a dose dependent manner reaching 50% inhibition at 10 nM.
Figure 4:
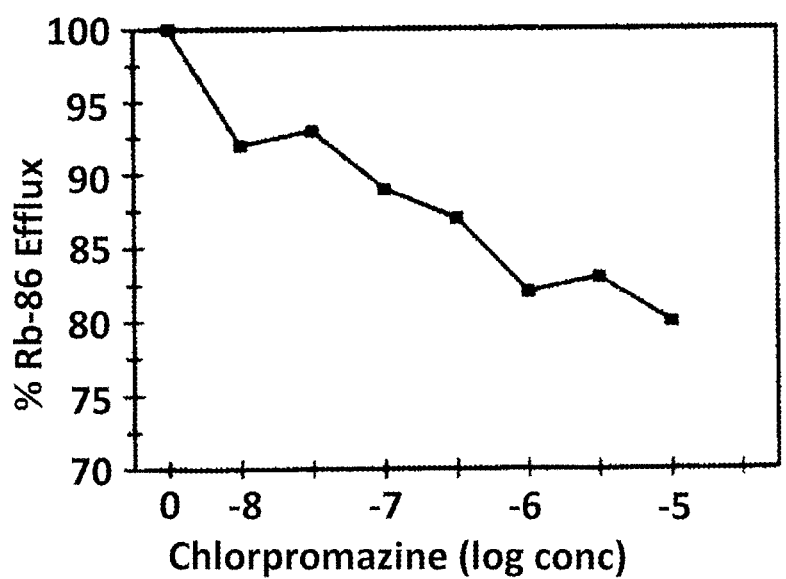
FIG. 4 depicts, in accordance with embodiments herein, effect of chlorpromazine on the efflux of $^{86}$Rb from human trabecular meshwork cell. Chlorpromazine inhibits $^{86}$Rb efflux in a dose dependent manner, but on a molar basis it is less effective than glybenclamide, reaching 20% inhibition at 1 μM.

To define whether the sulfonylurea receptor in trabecular meshwork cells is similar to the sulfonylurea receptor of pancreatic β-cells, the inventors compared the kinetics of displacement of $^3$H-glibenclamide by tolbutamide in bovine trabecular meshwork cells and RIN-m5F cells (an insulinoma cell line derived from rat pancreatic islet cells (ATCC® CRL-11605™). The data in FIG. 2 shows that the displacement of $^3$H-glibenclamide by tolbutamide from trabecular meshwork cells (green) and RIM-m5F (red) cells occurred with the same kinetics, suggesting that the receptors on the two cell lines have similar pharmacological properties.

Effect of Tolbutamide on IOP in Human Subjects.

a. Effect of 1 drop of 0.4% tolbutamide. Three patients with elevated IOP, due to exfoliative glaucoma, to POAG and to the increase in IOP that occurs in some patients following lens extraction, were treated with one drop of 0.4% tolbutamide solution. IOP was measured at "0" time and at one hour intervals for 5 hours (when possible) by a nurse while the patient was in the hospital. The results shown in Table 2, expressed as mm of Hg, show that tolbutamide can decrease IOP significantly in all three conditions of elevated IOP.

TABLE 2

Effect of one drop of 0.4% Tolbutamide on IOP Human Subjects

Figure 5:
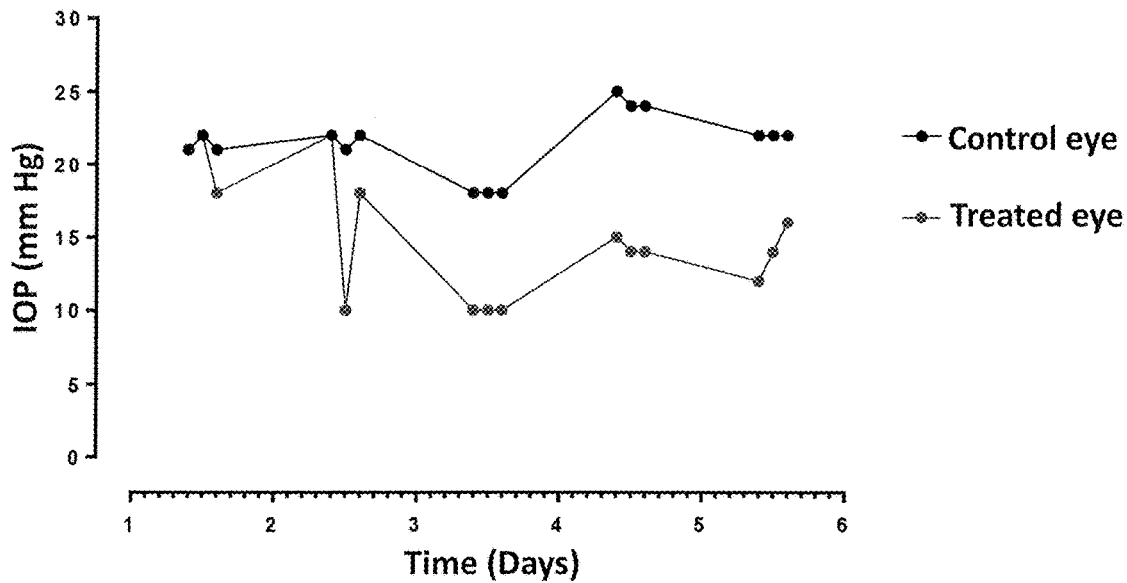
FIG. 5 depicts, in accordance with embodiments herein, long-term effect of 0.4% tolbutamide treatment on IOP of a human subject. Patient 1 suffered from high IOP with no visual field loss. On days 1 through 6 IOP was measured at 9:00 A.M., 1 drop of 0.4% Tolbutamide suspended in buffered PBS (pH 6.7) was instilled to the right eye and IOP measured at 12:00 Noon and at 3:00 P.M. The patient was instructed to apply one drop of drug 10:00 P.M. to the right eye and come to the clinic each day to have IOP measured. Note that during the first day the IOP remained high in this patient but decreased significantly during the next 5 days. The bottles were color-coded and the patient was not aware of which bottle contained the drug and which contained the vehicle. The patient and the technician measuring the patient's IOP was not aware of which bottle contained the drug and which contained the vehicle.

| | Patient | | | | |
|---|---|---|---|---|---|
| | 1 | | 2 | | 3 |
| | Disease | | | | |
| | Exfoliative Glaucoma of OD | | Primary Open Angle Glaucoma | | IOP Spike after Lens Extraction |
| | OD | OS | OD | OS | OD |
| "0" hours (pre treatment IOP) | 48 | 20 | 34 | 32 | 30 |
| 1 hr | | | 30 | 27 | |
| 2 hrs | 44 | 18 | | | 20 |
| 3 hrs | 32 | 14 | 26 | 22 | |
| 4 hrs | 30 | 14 | 22 | 20 | |
| 5 hrs | 30 | 14 | 22 | 20 | | b. Effect of 0.4% tolbutamide on human subjects for an extended time. To determine whether longer-term treatment with tolbutamide lowered IOP without any significant side effects, four patients with POAG patient was treated with one drop of 0.4% tolbutamide twice daily (FIGS. 5-7) as shown in the figures. Vials containing drug and vehicle were color-coded by the manufacturing facility; the patient, the nurse and the investigator were not aware which vial contained the drug and which vial contained the vehicle.

For patient 1, on days 1 through 6, IOP was measured at 9:00 A.M., 1 drop of 0.4% Tolbutamide suspended in buffered PBS (pH 6.7) was instilled to the right eye and IOP measured at 12:00 Noon and at 3:00 P.M. The patient was instructed to apply one drop of drag 10:00 P.M. to the right eye and come to the clinic each day to have IOP measured. Note that during the first day the IOP remained high in this patient but decreased significantly during the next 5 days.

Figure 6:
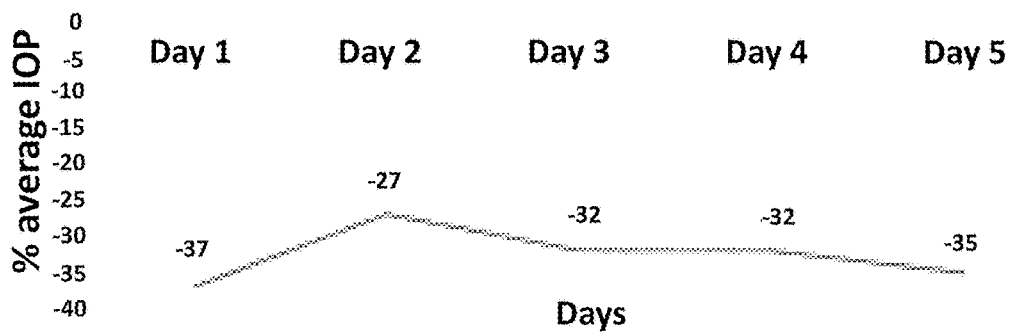
FIG. 6 depicts, in accordance with embodiments herein, Patient 2, who suffered from glaucoma and had become refractory to Timolol, was treated with 0.4% Tolbutamide after a 3-week washout. On days 1 through 5, IOP was measured at 8:00 A.M., 1 drop of 0.4% Tolbutamide suspended in buffered PBS (pH 6.7) was instilled to the right eye and IOP measured at the indicated times. A second drop was administered at 10:00 PM. All measurements and drug administrations were done in the hospital. The bottles were color-coded and the patient was not aware of which bottle contained the drug and which contained the vehicle. The patient and the technician measuring the patient's IOP was not aware of which bottle contained the drug and which contained the vehicle

As illustrated in FIG. 6 and Table 3, Patient 2, who suffered from glaucoma and had become refractory to Timolol, was treated with 0.4% Tolbutamide after a 3-week washout. On days 1 through 5, IOP was measured at 8:00 A.M., 1 drop of 0.4% Tolbutamide suspended in buffered PBS (pH 6.7) was instilled to the right eye and IOP measured at the indicated times. A second drop was administered at 10:00 PM. All measurements and drug administrations were done in the hospital, since the patient was admitted for an unrelated condition.

TABLE 3

| | | IOP OD (treated) | | OS (Control) | |
|---|---|---|---|---|---|
| Day | Time | mm Hg | % Change | mm Hg | % Change |
| 1 | 4:00 PM | 31 | | 16 | |
| | 6:00 PM | 21 | −32 | 13 | −19 |
| | 6:30 PM | 18 | −42 | 18 | +12 |
| 2 | 8:00 AM | 16 | −48 | 18 | +12 |
| | 4:00 PM | 27 | −13 | 18 | +12 |
| | 8:00 PM | 28 | −10 | 18 | +12 |
| 3 | 8:00 AM | 20 | −35 | 18 | +12 |
| | 4:00 PM | 22 | −29 | 16 | 00 |
| | 8:00 PM | 21 | −32 | 14 | −13 |

TABLE 3-continued

|     |         | IOP OD (treated) | | OS (Control) | |
| --- | ------- | ----- | -------- | ----- | -------- |
| Day | Time    | mm Hg | % Change | mm Hg | % Change |
| 4   | 8:00 AM | 18    | −42      | 19    | +19      |
|     | 4:00 PM | 22    | −29      | 13    | −19      |
|     | 8:00 PM | 24    | −23      | 15    | −6       |
| 5   | 8:00 AM | 17    | −45      | —     | —        |
|     | 2:00 PM | 23    | −26      | 19    | +19      |

Figure 7:
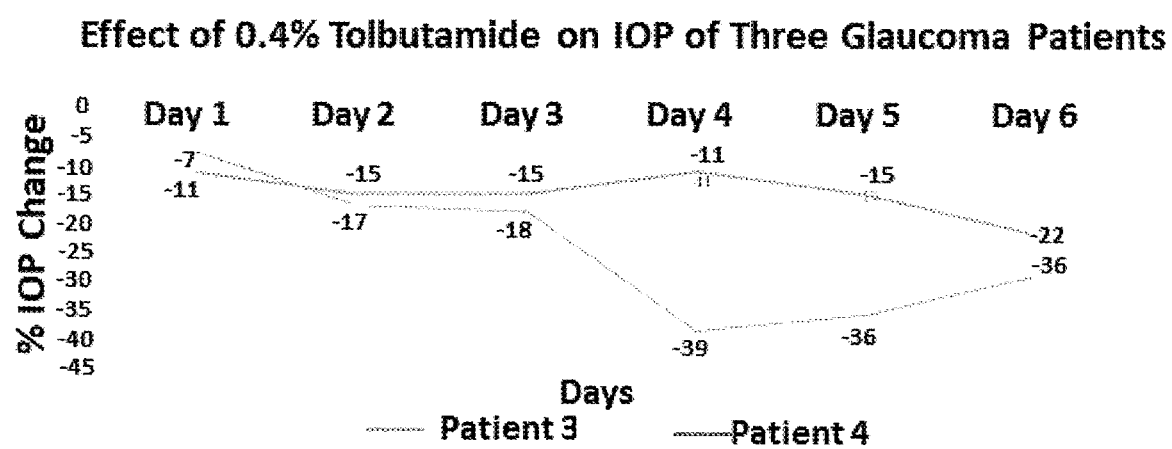
FIG. 7 depicts, in accordance with embodiments herein, long-term effect of 0.4% tolbutamide treatment on IOP of glaucoma patients. Patients 3 and 4 were given a bottle of drug and a bottle of control fluid (vehicle) and were instructed to instill one drop from one bottle in the right eye (drug) and one drop from the second bottle to the left eye (control) at 9:00 AM and at 10:00 PM. The patient was asked to come to the clinic at 8:30 AM and at 5:00 PM each day to have the IOP measured. The bottles were color-coded and the patient was not aware of which bottle contained the drug and which contained the vehicle. The patient and the technician measuring the patient's IOP was not aware of which bottle contained the drug and which contained the vehicle

Patients 3 and 4 were given a bottle of drug and one of vehicle and were instructed to instill one drop from one bottle in the right eye (drug) and one drop from the second bottle to the left eye (control) at 9:00 AM and at 10:00 PM. The bottles were color-coded and the patient was not aware of which bottle contained the drug and which contained the vehicle. The patient was asked to come to the clinic at 8:30 AM and at 5:00 PM each day to have the IOP measured (FIG. 7).

Effect of 0.4% tolbutamide on aqueous humor outflow facility: The unexpected results in the 5 glaucoma patients definitely show that inhibition of the ATP-sensitive potassium channel lowers IOP in open angle glaucoma patients, in exfoliative glaucoma patients as well as in patients with high IOP due to surgical intervention. Since Chowdhury has reported that activation of the ATP-sensitive channel promotes aqueous outflow in rodents, the inventors determined whether the lowering of IOP in glaucoma patients would be via a different mechanism. Thus, they investigated whether one drop of 0.4% tolbutamide would affect aqueous dynamics using fluorophotometry to measure aqueous production and outflow.

Fluorophotometry. To define the mechanism of action of tolbutamide, measurements of aqueous dynamics were done on patient 2 (See FIG. 6). For this study IOP and rate of aqueous formation were measured at 9:00 A.M. The patient was asked to apply one drop of drug to the right eye at 9:15 A.M. and one at 10:00 P.M. for 3 days. On the morning of the fourth day IOP and rate of aqueous formation were again measured.

TABLE 4

Effect of Tolbutamide on Inflow and Outflow of Aqueous Humor in a POAG Patient.

|               | Inflow (μl/min) | | Outflow Facility (μl/min/mmHg) | | IOP (mmHg) | |
| --- | --- | --- | --- | --- | --- | --- |
|               | OS  | OD  | OS    | OD    | OS | OD |
| Pre-Treatment | 2.1 | 1.9 | 0.161 | 0.146 | 22 | 22 |
| Post-treatment| 1.2 | 3.0 | 0.137 | 0.50  | 18 | 15 |

Facility of Outflow (C) was calculated after Goldman:

$$C = \frac{\text{Rate of formation}}{IOPt - \text{Episcleral } IOP},$$

where IOPt is the intraocular pressure in mmHg at the time the rate of inflow is measured. Episcleral pressure for this patient was estimated at 9 mmHg.

The results (Table 4) showing that KATP channel inhibition increase both production and outflow of aqueous were unexpected, considering that other researchers (such as Chowdbury et al) have not only reported that activation of the KATP channel decreases IOP in animal models of glaucoma and in perfused human anterior segment but that activation of the KATP channel by openers of the channels increase aqueous outflow. The present data shows that in glaucoma patients inhibition of the KATP channel increase aqueous production by 100% and increases aqueous outflow by 350%, suggesting that the KATP channel modulates the metabolic activity of the ciliary body/trabecular meshwork/Schlemm'canal complex. These data unquestionably show that KATP channel inhibition and not activation regulates aqueous humor dynamics.

Adverse ocular effects of tolbutamide administered as drops to the eye. To determine whether tolbutamide has any adverse ocular side effects, patients were observed for symptom of ocular toxicity. Specifically, patients were monitored for discomfort, ocular pain, tearing, photophobia, erythema, swelling, discharge and scaling, palpebral conjunctival inflammation, bulbar conjunctival inflammation; limbal inflammation, corneal epithelial changes and focal stromal infiltrates. Symptoms were classified as 0=normal; 1=mild; 2=moderate; and 3=severe. All patients in the study were found to be free of any symptoms at any time during the study. In all cases symptoms were classifies as "0".

Example 6

Additional Experimental Results and Discussion

In one embodiment, the gene for the KATP channels is mutated. Specifically, the inventors isolated trabecular meshwork cells from donor eyes that had a history of glaucoma; the genes for both subunits of the channel, the pore forming subunits, KCNJ8 and KCNJ11, and the sulfonylurea subunit, ABCC8 and ABCC9, were sequenced and compared to the sequence to publicly available data to determine specific mutations. The methods of the present disclosure are intended for the diagnosis and identification of individuals at risk within a population.

The KATP channels, members of the inward rectifying K+ channel family, are octameric complexes composed of four Kir6.x subunits and four SUR subunits. The Kir6 subfamily is a member of the inward rectifier family and has two members, Kir6.1 and Kir6.2. SURs are members of the ABC superfamily and comprise sulfonyl urea receptors SUR 1, SUR 2A and SUR 2a SURs, by themselves, perform no recognized function. Instead, they undergo association with heterologous pore-forming subunits to form ion channels, which they regulate. SUR1 contains two nucleotide-binding domains as well as low and high affinity binding sites for sulfonylurea drugs and related compounds. Drugs such as glibenclamide, tolbutamide and glinides are potent inhibitors of SUR-regulated channel activity. SURs are the target of sulfonylurea drugs and glinides used to treat diabetes mellitus type 2, neonatal diabetes, and some forms of congenital hyperinsulinemia. In the pancreatic β-cells binding of sulfonylureas and glinides to KATP channels induces channel closure, causing membrane depolarization, which activates voltage-dependent $Ca^{2+}$ channels in the β-cell plasma membrane and the resulting $Ca^{2+}$ influx triggers $Ca^{2+}$-dependent insulin granule exocytosis.

Example 7

Mutation Results

In the eye intraocular pressure (IOP) is maintained by an equilibrium between aqueous production by the ciliary body and aqueous outflow via the trabecular meshwork-Schlemm's canal complex. In approximately 60% of primary open angle glaucoma (POAG) patients IOP increases because of a decrease in aqueous outflow; however, in about 40% of glaucoma patients the IOP is normal. It is worth noting that in patients with high IOP less than 20% develop glaucoma 5 years after high IOP diagnosis (Gordon M O, Torri V, Miglior S, et al. Ocular Hypertension Treatment Study Group; European Glaucoma Prevention Study Group. Validated prediction model for the development of primary open-angle glaucoma in individuals with ocular hypertension. Ophthalmology. 2007; 114:10-90) Therapeutic agents for the treatment of open angle glaucoma, whether patients have high or normal IOP include prostaglandin analogs, β-adrenergic receptor blockers, αβ-adrenergic receptor blockers, α1-adrenergic receptor blockers, α2-adrenergic receptor agonists, and carbonic anhydrase inhibitors. These drugs lower IOP be increasing uveoscleral outflow or by decreasing aqueous production. Rhepressa, a drug soon to be on the market, increases outflow via the trabecular meshwork-Schlemm's canal complex. When pharmacological agents are no longer effective at lowering IOP sufficiently, surgical intervention is necessary. It should be noted that even when drugs are effective at lowering IOP, retinal ganglion cells continue to undergo apoptosis and consequently vision loss progression, albeit at lower rate.

Research of the inventors have shown that sulfonylureas and glinides, which are inhibitors of the ATP-sensitive potassium channels, lower intraocular pressure significantly. As disclosed herein, their studies in humans have shown that 0.4% tolbutamide lowers intraocular pressure from 25-50% in primary open angle glaucoma patients, in exfoliative glaucoma patients and prevents the IOP spike that occurs following cataract surgery. When outflow was examined via the trabecular meshwork-Schlemm's canal complex the inventors found that 0.4% tolbutamide increases aqueous production by 150% and increases outflow by 350%, a net 200% outflow increase. Since it is known that with normal aging aqueous humor production decreases, these results suggest that tolbutamide rejuvenates the ciliary body-trabecular meshwork-Schlemm's canal complex.

KATP channels are hetero-octameric complexes comprised of four pore-forming inward rectifier potassium channel subunits (Kir6.1 or Kir6.2) and four regulatory sulfonylurea receptor subunits (SUR1 or SUR2). Kir6.1 and Kir6.2 are encoded by the genes KCNJ8 and KCNJ11, whereas SUR1 and SUR2 are encoded by ABCC8 and ABCC9, respectively. The inventors sequenced the 4 genes in 9 glaucoma patients and found that in all 9 patients the KCNJ11 gene had a nonsense mutation (rs5215) that resulted in the substitution of isoleucine for valine at position 337 (V337I) in the Kir6.2 protein resulting in loss of channel function defined as a mutation that results in reduced or abolished protein function; the KCNJ11 gene also had the nonsense mutation (rs5219) that resulted in the substitution of glutamic acid for lysine at position (E23K), which has been associated with type 2 diabetes, resulting in loss of channel function defined as a mutation that results in reduced or abolished protein function. The loss of channel function resulting from the V337I and E23K mutations signifies that in glaucoma patients closure of the channel, which is normally mediated by ATP, requires higher concentrations of ATP than the concentration required in normal patients. In individuals that carry the mutations, the slower metabolism and lower ATP concentration that occurs with age would lead to glaucoma. The mutations suggested that that in trabecular meshwork the channel was comprised of SUR1/ or SUR2/Kir6.2.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating glaucoma in a patient, wherein the patient has a nonsense mutation rs5215 in the KCNJ11 gene and wherein the patient does not have diabetes, comprising:
   identifying the patient having nonsense mutation rs5215 in the KCNJ11 gene, and wherein the nonsense mutation rs5215 codes for the Kir 6.2 protein and replaces Valine with Isoleucine at position 337 (V337I) of the Kir 6.2 protein;
   administering to the patient upon identification of the mutation, a composition comprising a therapeutically effective amount of tolbutamide or a physiologically equivalent salt or solvate thereof and a pharmaceutically acceptable carrier, and
   wherein tolbutamide is at a concentration of 0.1-0.9% (w/v).

2. The method of claim 1, wherein the presence of a mutation is determined using a single nucleotide polymorphism (SNP) genotyping method.

3. The method of claim 1, wherein the pharmaceutically acceptable carrier is an ophthalmically acceptable carrier.

4. The method of claim 1, wherein the dosages are administered from 1 to 4 times per day.

5. The method of claim 1, wherein the method further comprises administration by topical application to the eye.

6. The method of claim 1, wherein the method further comprises administration by injection into the anterior chamber of the eye.

7. The method of claim 1, wherein the method further comprises administration using an ocular insert.

8. The method of claim 1, wherein administration of the tolbutamide increases aqueous humor production by at least 100%.

9. The method of claim 1, wherein administration of the tolbutamide increases aqueous outflow by at least 150%.

10. The method of claim 1, wherein the glaucoma is normal tension open angle glaucoma.

11. A method of diagnosing and treating glaucoma in a subject who does not have diabetes, comprising:
    obtaining a biological sample from the subject;
    testing the biological sample for presence of a mutation in Kir6.2 protein or KCNJ11 gene; and
    diagnosing and treating glaucoma in the subject upon determining the presence of a mutation in Kir6.2 protein or KCNJ11 gene; and
    wherein the mutation replaces Valine with Isoleucine at position 337 (V337I) of the Kir 6.2 protein.

12. The method of claim 11, further comprising treating glaucoma by administering to the subject a composition comprising a therapeutically effective amount of tolbutamide or a physiologically equivalent salt or solvate thereof and a pharmaceutically acceptable carrier.

13. A method of treating ocular hypertension in a normal or glaucomatous subject, wherein the subject has a nonsense mutation rs5215 in the KCNJ11 gene and does not have diabetes, comprising:
    administering to the patient a therapeutically effective amount of a composition comprising tolbutamide, sulfonylurea, and/or glinide, or a physiologically equivalent salt or solvate thereof, and a pharmaceutically acceptable carrier,
    wherein the nonsense mutation rs5215 codes for the Kir 6.2 protein and replaces Valine with Isoleucine at position 337 (V337I) of the Kir 6.2 protein.

14. The method of claim 13, wherein the ocular hypertension is reduced by at least 20%.

15. The method of claim 13, wherein the pharmaceutically acceptable carrier is an ophthalmically acceptable carrier.

* * * * *